United States Patent [19]

Liston et al.

[11] Patent Number: 4,600,412
[45] Date of Patent: Jul. 15, 1986

[54] WATER SEPARATOR

[75] Inventors: Max D. Liston, Irvine; James R. Braig, El Toro; Wayne Blackburn, Irvine; Paul Hsei, Huntington Beach, all of Calif.

[73] Assignee: Datascope Corporation, Oakland, N.J.

[21] Appl. No.: 659,097

[22] Filed: Oct. 9, 1984

[51] Int. Cl.$^4$ ............................................. B01D 45/00
[52] U.S. Cl. .......................................... 55/189; 55/270; 55/392; 55/426
[58] Field of Search .............. 55/189, 171, 270, 392, 55/426, 434, 319

[56] References Cited

U.S. PATENT DOCUMENTS

| | | | |
|---|---|---|---|
| 1,915,408 | 6/1933 | Crossen | 55/434 X |
| 3,834,136 | 9/1974 | Dussourd et al. | 55/189 X |
| 3,944,399 | 3/1976 | Gspann | 55/392 X |
| 3,952,781 | 4/1976 | Hiller et al. | 55/189 X |
| 4,099,939 | 11/1978 | Vancheri et al. | 55/270 X |
| 4,140,005 | 2/1979 | Kittelson | 55/270 X |
| 4,304,578 | 12/1981 | Hakala et al. | 55/189 |

FOREIGN PATENT DOCUMENTS 0709114 1/1980 U.S.S.R. ..................... 55/189

Primary Examiner—Charles Hart
Attorney, Agent, or Firm—Darby & Darby

[57] ABSTRACT

A water separator adapted for use in a gas monitor includes a gas inlet port, a gas outlet port, a two-stage gas/water separator section, and a fluid reservoir. The two-stage gas/water separator section includes a first portion defining a first chamber which communicates with the gas inlet and gas outlet ports via a connecting conduit, a second portion defining a second chamber which communicates with the first chamber and the fluid reservoir, and an intermediate portion interposed between the first and second portions and defining a constricted passage between the first and second chambers. The second chamber has a frusto-conical shape in longitudinal cross section.

12 Claims, 3 Drawing Figures

WATER SEPARATOR

BACKGROUND OF THE INVENTION

1. Field of the Invention

This invention relates to an improvement in the design of a water separator particularly for use in a monitor for sampling and analyzing gas exhaled by a patient, or more generally for use in other devices where water must be separated from a gas.

2. Description of the Prior Art

Many gas analyzers on the market today require water separators to remove water from the air exhaled by a patient. An example of such a device is disclosed in U.S. Pat. No. 4,382,806 (Hakala, et al.). The water separator, or "water trap" as it is commonly referred to, disclosed in the Hakala, et al. patent includes a downwardly pointing tube which opens into the interior of a cuvette, as illustrated in FIG. 1 of the drawings of that patent.

The water trap disclosed in the Hakala, et al. patent appears to be a typical and conventional design and quite useful in many applications where water is to be separated from the sampled gas.

OBJECTS AND SUMMARY OF THE INVENTION

It is an object of the present invention to provide a new and improved design for a water separator or water trap for use in a gas monitor or other device.

In accordance with the present invention, a water separator for use in a gas analyzer or monitor includes a housing which is formed with a gas inlet port and a gas outlet port, a reservoir for holding condensed moisture and a two stage gas/water separator section. The gas/water separator section includes upper and lower portions and an intermediate portion interposed between the upper and lower portions. The upper portion of the separator section defines a first interior chamber which communicates with the gas inlet and gas outlet ports. Likewise, the lower portion defines a second interior chamber which communicates with the first chamber and the fluid reservoir. The intermediate portion defines a constricted passage between the first and second chambers. The water reservoir is joined to the lower portion of the separator section and collects the condensed water vapor from the air exhaled by the patient.

The bottom of the first chamber is preferably flat. The second chamber has an overall frusto-conical shape in longitudinal cross-section. The particular shape of the separator section lends itself favorably to the efficient separation of water from the air exhaled by the patient.

These and other objects, features and advantages of this invention, will be apparent from the following detailed description of illustrative embodiments thereof, which is to be read in connection with the accompanying drawings.

DETAILED DESCRIPTION OF THE PREFERRED EMBODIMENTS

Figure 1:
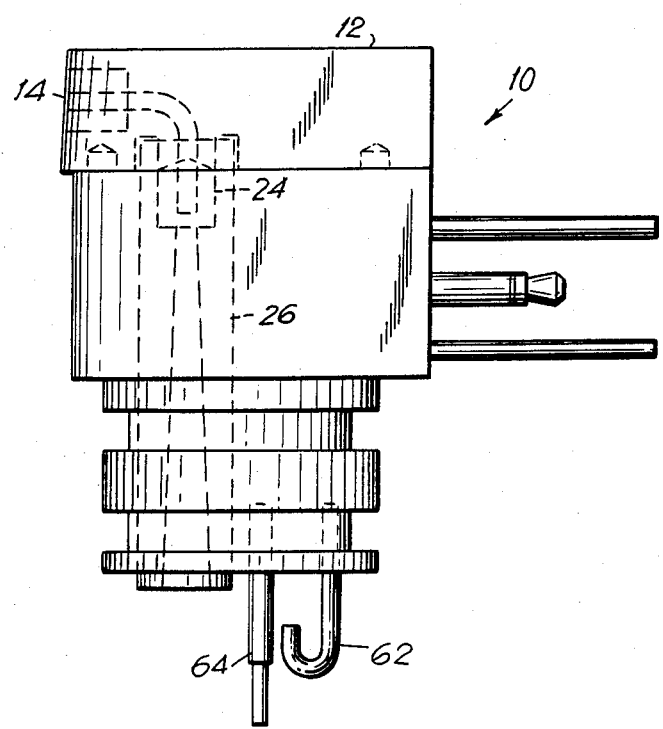
FIG. 1 is a section view of a water separator constructed in accordance with the present invention.
Figure 3:
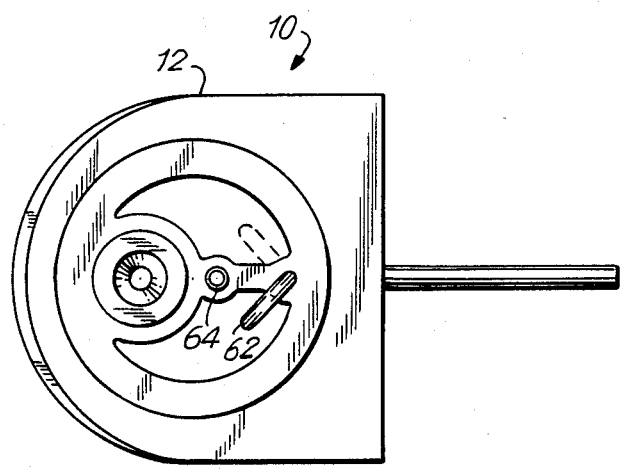
FIG. 3 is a section view of the water separator illustrated by FIG. 1 and taken along the line 3—3.
Figure 2:
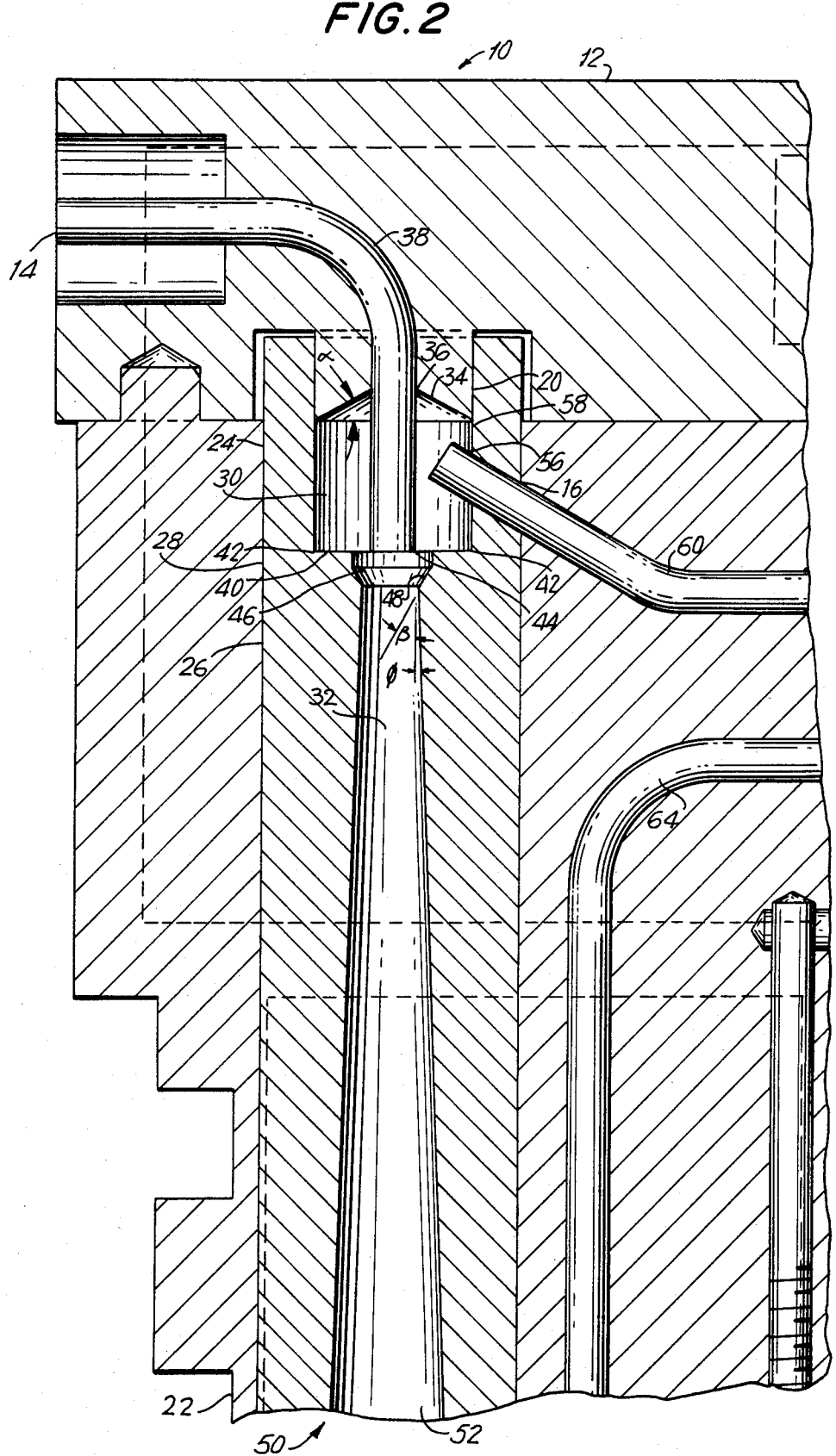
FIG. 2 is an enlarged detailed view of the water separator of the FIG. 1.

Referring initially to FIGS. 1-3 of the drawings, it will be seen that a water separator 10 adapted for use in a gas monitor or analyzer includes a housing 12 which is formed with a gas inlet port 14 and a gas outlet port 16. The gas inlet port 14 is connected to the patient's breath sample tube or catheter 18, and the gas outlet port 16 is connected to a gas monitor, although it is envisioned that other types of analyzers or devices may suitably use the water separator.

The water separator further includes a two-stage gas/water separator section 20, and a fluid reservoir 22.

The two-stage gas/water separator section 20 is divided into a first portion 24 and a second portion 26 preferably positioned as upper and lower segments, respectively, and an intermediate portion 28 interposed between the first and second portions.

The first portion 24 of the separator section defines a first chamber 30 in its interior which is in communication with the gas inlet and gas outlet ports 14,16, and which receives the air exhaled by the patient. The second portion 26 defines a second chamber 32 in its interior which communicates with the first chamber 30 and the fluid reservoir 22.

The first chamber 30 defined by the first portion is preferably cylindrical in shape. The first portion 24 may include a conically peaked interior upper surface 34, which defines a ceiling for the first chamber 30, that defines an angle $\alpha$ of about 30° with the horizontal. The upper surface has a centrally located opening 36 formed therein. This opening 36 is dimensioned to receive a conduit 38 which connects the gas inlet port 14 of the device with the first portion 24 of the separator section so that the gas inlet port 14 and the first chamber 30 are in communication. Also, this conduit extends slightly into the interior of the first chamber 30 a short distance below the upper interior surface of the first portion.

The lower interior surface 40 of the first portion is also cylindrically shaped and may include sharp corners 42 to define a flat bottom for the first chamber 30. The lower interior surface 40 has an opening 44 formed centrally therein which is aligned with and positioned below the end of the connecting conduit 38.

Disposed adjacent to and beneath the opening 44 formed in the lower interior surface of the upper portion is the intermediate portion 28 of the separator section. The intermediate portion defines a constricted passage 46 between the first and second chambers 30,32 of the separator section. This constricted passage 46 may be formed by the intermediate portion having tapered side walls 48 which form an angle $\beta$ with the vertical of about 30°.

The second portion 26 of the separator section is disposed below the intermediate portion 28 and adjacent thereto. The second chamber 32 of this portion extends from the constricted passage 46 of the intermediate portion, and progressively widens to the lower end 50 of the second portion to provide the second chamber with an overall frusto-conical shape in longitudinal section. The lower end 50 of the second portion has formed therein an opening 52 for discharge of condensed moisture to the fluid reservoir 22.

It should be noted here that although the separator section has been defined in terms of a first, second and intermediate portion, it is clearly obvious that what is important in the design of the separator section is the shape of the first and second chambers 30,32 and the constricted passage 46 joining the two, in that these shapes may be provided with a separator section having integrally formed portions.

As mentioned previously, the second chamber 32 of the second portion widens progressively in the direction of its lower end. The interior walls 54 of the second portion preferably diverge from the longitudinal axis of the second portion to form an angle $\phi$ with the longitudinal axis of about 2°.

The first chamber 30 also includes a second opening 56 formed in the interior side wall 58 of the first portion. The second opening 56 is dimensioned to receive a conduit 60 which connects to the gas outlet port so that the gas outlet port 16 and the first chamber 30 are in communication. The conduit connecting the gas outlet port 16 with the first chamber 30 preferably forms an angle 0 of about 60° with the longitudinal axis of the first portion, and projects into the interior of the first chamber 30 a short distance.

The water separator or water trap 10 of the present invention may also include a sump moisture vacuum conduit 64 which extends into the fluid reservoir 22. This conduit 64 creates a partial vacuum in the reservoir to help draw the water out of the chambers of the separator section and into the fluid reservoir. If desired, the water trap may also include an electrode 62 extending partially into the reservoir 22. This electrode 62, which includes an axial conduit and a concentrically disposed outer conductor, is used to signal the gas monitor when the reservoir is full.

The reservoir 22 is disposed below the second portion of the separator section and adjacent thereto. It is of conventional design and is preferably formed of clear plastic to facilitate visual inspection and monitoring of the moisture which accumulates therein.

The water separator 10 of the present invention works in the following manner. The patient's catheter is attached to the gas inlet port of the water separator. Air exhaled by the patient is received by the water separator through the gas inlet port and flows through the connecting conduit to the first chamber 30 of the separator section, where partial separation of water carried by the exhaled air occurs.

The exhaled air also flows into the second chamber 32 of the separator section where additional water is separated and condensed. The gas sample, with substantially no water, flows out of the first chamber 30 through the air outlet conduit and to the gas outlet port of the water separator. This gas sample, now free of almost all water, is ready for analysis by a gas monitor.

The large capacity, two-stage water separator 10 of the present invention maintains a high frequency response while providing sufficient capacity for several days of continuous monitoring. It satisfactory separates water from the patient's gas and is adapted for use in gas analyzers and other instruments.

Although the illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A water separator adapted for use with a gas analyzer, which comprises:

a housing being formed with a gas inlet port and a gas outlet port, the housing having a first chamber formed therein, the housing including an upper interior surface defining the upper extent of the first chamber, and a lower interior surface defining the lower extent of the first chamber, the lower interior surface having a central opening formed therein, the upper interior surface having a peaked shaped;

a gas inlet conduit communicating with the gas inlet port and extending at least from the upper interior surface partially into the first chamber, the gas inlet conduit having an end positioned above and aligned with the central opening formed in the lower interior surface;

a gas outlet conduit communicating with the gas outlet port and extending partially into the first chamber; and a fluid reservoir communicating with the central opening formed in the lower interior surface for collecting water.

2. A water separator as defined in claim 1 which further includes a vacuum conduit extending into the fluid reservoir.

3. A water separator as defined by claim 1, wherein the housing further includes a second chamber formed therein and disposed below and in communication with the first chamber through the central opening formed in the lower interior surface.

4. A water separator as defined by claim 3, wherein the housing includes an interior lower side wall which defines the lateral extent of the second chamber, the interior lower side wall forming an interior angle with the longitudinal axis of the second chamber of about two degrees.

5. A water separator as defined in claim 3 wherein the second chamber has an overall frusto-conical shape in longitudinal cross section.

6. A water separator as defined by claim 1, wherein the lower interior surface is flat.

7. A water separator as defined by claim 3, wherein the housing further includes an intermediate portion interposed between the first and second chambers and communicating with the first and second chambers and the central opening formed in the lower interior surface, the intermediate portion defining a constricted passage between the first and second chambers.

8. A water separator as defined in claim 7 wherein the intermediate portion includes tapered side walls defining the constricted passage and wherein the tapered side walls form an interior angle with the longitudinal axis of the intermediate portion of about 30°.

9. A water separator as defined by claim 1, wherein the upper interior surface forms an interior angle with the longitudinal axis of the first chamber of about 60 degrees.

10. A water separator as defined by claim 1, wherein the housing includes an interior upper side wall which defines the lateral extent of the first chamber; and wherein the gas outlet conduit extends partially into the first chamber through the interior upper side wall.

11. A water separator as defined by claim 10, wherein at least the portion of the gas outlet conduit which extends into the first chamber is disposed at about 60 degrees to the longitudinal axis of the first chamber.

12. A water separator as defined by claim 1, which further includes means for sensing the presence of water in the fluid reservoir.

* * * * *